(12) United States Patent
Fuisz et al.

(10) Patent No.: US 8,241,661 B1
(45) Date of Patent: Aug. 14, 2012

(54) BIOCOMPATIBLE FILM WITH VARIABLE CROSS-SECTIONAL PROPERTIES

(76) Inventors: Richard C. Fuisz, Beverly Hills, CA (US); Joseph M. Fuisz, Surfside, FL (US)

( * ) Notice: Subject to any disclaimer, the term of this patent is extended or adjusted under 35 U.S.C. 154(b) by 0 days.

(21) Appl. No.: 13/168,576

(22) Filed: Jun. 24, 2011

(51) Int. Cl.
*A61F 13/00* (2006.01)
*A61K 9/70* (2006.01)

(52) U.S. Cl. ........................................................ 424/443

(58) Field of Classification Search ............................ None
See application file for complete search history.

(56) References Cited

U.S. PATENT DOCUMENTS
2004/0258896 A1* 12/2004 Yang et al. ..................... 428/220

FOREIGN PATENT DOCUMENTS
WO WO 2008/056001 A1 * 5/2008

OTHER PUBLICATIONS

Li et al., "Latex Film Matrix Systems with a Concentration Gradient for Controlled Drug Delivery" Drug Development and Industrial Pharmacy, 1991, vol. 17, No. 15, pp. 2041-2054.*

* cited by examiner

*Primary Examiner* — James H. Alstrum-Acevedo
*Assistant Examiner* — Daniel L Branson
(74) *Attorney, Agent, or Firm* — Antonelli, Terry, Stout & Kraus, LLP.

(57) ABSTRACT

A biocompatible film includes a single layer having a plurality of components, at least one of the plurality of components having a predetermined non-uniform distribution in the thickness direction of the single layer. The at least one of the plurality of components that has a non-uniform distribution in the thickness direction of the single layer may have a substantially uniform distribution in the longitudinal and lateral directions of the single layer. The biocompatible film can be made by depositing a fluid composition including a film forming material and at least one other component immiscible with the film forming material and having a density different than the film forming material into a single layer, and drying the single layer such that the at least one other component has a predetermined non-uniform distribution in the thickness direction of the single layer after drying.

31 Claims, No Drawings

BIOCOMPATIBLE FILM WITH VARIABLE CROSS-SECTIONAL PROPERTIES

BACKGROUND OF THE INVENTION

The use of thin films and sheets in drug delivery has developed and matured over the past years. The initial commercial application in the United States was introduced by Prestige Brands with a benzocaine containing strip marketed under its Chloraseptic® brand. Novartis followed with cough and cold drugs (including the actives dextromethorphan and diphenhydramine) under its Triaminic® brand. Others have followed, including in the ethical drug space, e.g. Meda/Biodelivery Sciences' Onsolis® and Reckitt Benckiser's Suboxone®.

The use of thin films and sheets for buccal and sublingual delivery is a promising area for drug delivery due to, inter alia, the avoidance of first pass metabolism. For such products, it is has been shown that it is desirable to reduce or eliminate the amount of drug which is transported via salivary flow to the GI tract. This observation is, of course, correct. Where the intention is to use buccal, sublingual or other mucosal surface delivery to avoid first pass effect (or for other reasons), one wants to maximize the drug available for absorption at the intended mucosal delivery site and minimize the amount of drug that is available at unintended delivery sites (the GI tract) where first pass metabolism will not be avoided. See Fuisz U.S. Patent Application Publication No. 20090098192 A1 discussing salivary flow, the content of which is hereby incorporated by reference in its entirety.

A known solution to this issue is the use of a bi layer film or sheet. In one embodiment a soluble film layer containing drug is backed by a second insoluble (or less soluble) layer without active drug. A commercial example of this is the Onsolis® product by Biodelivery Sciences International. The less soluble backing layer protects the drug layer from salivary flow dissolution, thereby increasing the degree of drug available for buccal absorption and decreasing the loss of drug to salivary distribution.

Thus, the desirability of bilayer and multilayer film and sheet systems is understood. However, practitioners will appreciate that such systems are more difficult and costly to manufacture than a single layer film or sheet. Typically, two films must be made and then laminated (see Tapolsky U.S. Pat. No. 7,579,019, the content of which is hereby incorporated by reference in its entirety). Or, one may manufacture one film and then cast a second layer on top of it (see Schmidt U.S. Pat. No. 4,849,246, the content of which is hereby incorporated by reference in its entirety). Of these two methods, it appears the Tapolsky method has gained far more traction in terms of actual commercial practice. Either way however, methods involve greater expense and additional steps as compared with single layer film production.

SUMMARY OF THE INVENTION

A biocompatible film includes a single layer having a plurality of components, at least one of the plurality of components having a predetermined non-uniform distribution in the thickness direction of the single layer. The at least one of the plurality of components that has a non-uniform distribution in the thickness direction of the single layer may have a substantially uniform distribution in the longitudinal and lateral directions of the single layer. The biocompatible film can be made by depositing a fluid composition including a film forming material and at least one other component immiscible with the film forming material and having a density different than the film forming material into a single layer, and drying the single layer such that the at least one other component has a predetermined non-uniform distribution in the thickness direction of the single layer after drying.

DETAILED DESCRIPTION OF THE INVENTION

It would be of obvious benefit to manufacture a single layer biocompatible film with multilayer characteristics of varying dissolutive properties, using the same process as is used to manufacture a single layer film but this is not possible using the existing art. However, the current inventors posit the manufacture of a single layer product using a single layer casting process that results in a product with variable cross-sectional dissolution capability. In one embodiment of the present invention, this results in a wet cast film with domains of slower dissolving material on one side, such that the product can be used with the faster dissolving side against the oral mucosa and the slower dissolving material side is retardant to salivary flow (akin to, but distinct from, a bi-layer film) and conceivably in the reverse.

In the prior art, Fuisz et al. dealt with a cast film that purposely contain a uniform distribution of components (See, U.S. Pat. Nos. 7,357,891; 7,425,292; 7,666,337; 7,824,588; and 7,897,080, the content of each of which is hereby incorporated by reference in its entirety).

U.S. Pat. No. 7,357,891 describes its invention thusly: "These films provide a non-self-aggregating uniform heterogeneity of the components within them by utilizing a selected casting or deposition method and a controlled drying process." U.S. Pat. No. 7,425,292 similarly describes "a process for preparing a film with a substantially uniform distribution of components" and indeed requires "a substantially uniform distribution of components" as part of claim 1 thereto. U.S. Pat. No. 7,666,337 contains the same language in the body and in claim 1 thereto: "a substantially uniform distribution of components." U.S. Pat. No. 7,824,588, again, provides as follows: "These films provide a non-self-aggregating uniform heterogeneity of the components within them." And finally, U.S. Pat. No. 7,897,080 has similar disclosures, notes that agglomerates can randomly distribute film components in the films of U.S. Pat. No. 4,136,145, and requires as part of claim 1 thereto, "a substantially uniform distribution of components."

In the present invention, the uniformity of components is done away with in a predetermined manner that is novel and has great utility. By dint of having a non uniform distribution of certain components, the application opens the way for a new type of cast film, particularly in but not limited to buccal and sublingual use. The present invention uses non/less miscible and/or density dissimilar components to produce a desired or predetermined non uniform distribution of components whereby the non/less miscible and/or different density components aggregate to form cross-sectional (i.e., through a plane parallel to the thickness direction) domains. Miscibility and/or density gradients result in a domain relegation in the film that is superior or inferior in a specific geography—typically the top or the bottom—of the film. This allows for one side of the film to be less affected by salivary degradation in favor of the more effective buccal and sublingual absorption.

Uniformity of bioactive per dosage unit is retained. Stated another way, we achieve a film that functions as multi-layer film but one that is made using a single layer process. While the film has a predetermined non uniform distribution of components, it has a uniformity of bioactive content in the dosage unit when each dose is cut from the master roll (it being understood that film dosage units are cut by surface area or mass—doses are not cut from the master roll as cross sections). It would be understood that this dosage unit will have application to the confection industry for long flavor delivery and/or the delivery of staged multiple flavors.

Stated another way, in U.S. Pat. No. 7,897,080, the natural phenomenon of Stoke's law is employed—through control of viscosity of the base solution—to retard the rate of sedimentation so as to allow the film to be dried prior to sedimentation from occurring. Sedimentation was to be avoided to, inter alia, prevent a non-uniform dispersion of components and active (See, U.S. Pat. No. 7,897,080 starting at column 7, line 55). In the present invention, we invite sedimentation to create the domains within the film's geographic cross section that give us the desired film properties. At the same time, we avoid any loss of the uniformity of the bioactive in the dosage unit itself.

Apart from buccal and sublingual use, we envision vaginal use where flows of bodily fluids must be dealt with. Similarly, we envision use for wound care, intra-nasal, topical and other forms of drug delivery.

We expressly contemplate the use of the film of the present invention in combination with, or as part of, a medical device. For example, the film of the present invention may be adhered to a tampon to deliver drug while also creating a barrier between vaginal fluid flow and the absorbent material of the tampon. The film of the present invention may also be adhered to a teabag like paper or other substrate for flavor or other delivery purpose.

Despite the predetermined non-uniformity of components, we demonstrate an ability to maintain uniformity of drug content. Drug uniformity is maintained in the dosage unit itself with little concern for the necessity of uniform components distribution in the dosage unit. This is accomplished by using miscibility differences in the cast film liquid phase and/or use of different densities of non soluble materials which quickly form differing domains along the thickness direction in the film as cast. This is then exposed to a drying process. This use of immiscible as a relative or true factor, combined with a density gradient to form domains in the end product and therefore a non uniform distribution of components which distinguishes this product and method from the prior art.

There need not be a uniformity of geographic distribution of the bioactive in the individual dosage unit for it to be uniform in the entirety of the dosage form.

This single layer cast thin film has multiple cross sectional domains along the thickness direction which allow for a gradient of hydrophilicity or hydrophobicity relevant to the contact portion with the mucosa and the salivary available portion for which dissolution is less desirable in a buccal film.

Hollow microspheres provide one possible means of modifying the density and solubility of a variety of compounds and they are used to form domains of various components including, inter alia, nano groups, cyclodextrins and particles. Apart from hollow spheres, other containment vessels, or alone, or with ion exchange resins, that have the requisite miscibility/solubility, density gradient required in this system.

The present invention also allows for being a multidrug and/or precursor film through differences in drug distribution in the cross section of the films variable miscibility and or density. This is augmented by the capability to have multiple domains in a single film. This is accomplished by varying drug solubility's and absorption states matched with the segregated components of this type of film. Furthermore, by the use of different degrees of solubility, sustained release, in mucosal as well as GI swallowed delivery is now made possible.

Also sustained release film is made possible through the differences in dissolution of the non uniform components of the film. The invention can be used for decreased salivary dissolution in a buccal or sublingual dosage unit. Similarly, the invention can be used for decreased vaginal fluid dissolution in a mucosal dosage unit.

The examples will demonstrate to one skilled in the art that the relationship of bioactive agent to the film or deposition can be, without limitation, (a) at least one bioactive agent in all domains, (b) at least one bioactive agent in one domain, (c) at least one bioactive agent in one but not all domains, (d) multiple bioactive agents in all domains, (e) multiple bioactive agents in one but not all domains, (f) multiple bioactive agents in all domains and (g) combinations of all the foregoing.

The biocompatible film can be made by a method comprising depositing a fluid composition including a film forming material and at least one other component immiscible with the film forming material and having a density different than the other film forming material into a single layer, drying the single layer such that the at least one other component has a predetermined non-uniform distribution in the thickness direction of the single layer after drying.

In addition to wet casting a master roll, the inventive material can be metered into a unit dose well by a ktronic or other metering device and dried in situ to form a unit dose dosage form with the same result as in the cast film. The well deposition is a convenient methodology for unit dosage units (see examples M-O of U.S. Pat. No. 7,824,588).

Coating or casting methods are particularly useful for the purpose of forming the films of the present invention. Some, but not limiting, examples include reverse roll coating, gravure coating, immersion or dip coating, metering rod or Meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife.

In the curtain coating process, a bath with a slot in the base allows a continuous curtain of the coating to fall into the gap between two conveyors. The object to be coated is passed along the conveyor at a controlled speed and so receives the coating on its upper face.

While extrusion is well know as a method of making sheet and films, the inherent mixing forces of that process make it possible but less desirably suited to the manufacture of the present invention.

The application of one or all immiscible layers may take place at any stage in the manufacturing process but will be guided by one skilled in the art by placement varying, based on rheology, from the initial mother mix to the daughter mixer stage to the stage beyond the daughter mixer and just prior to the cast (See U.S. Pat. No. 7,666,337 FIG. 6).

A slight delay in the application of heat may be desirable—from 0.001 second to up to 2 minutes, preferably 0.001 to 1.5 minutes—to allow for domain formation before the evaporation of the solvent begins to heighten the viscoelastic properties of the matrix. Uniform drying oven heat may be used without the need for preferential initial bottom heat, as is practiced in some prior art methods.

The domain forming agent may be any immiscible agent. Preferably, it will have a density higher or lower than the film forming main matrix. Hydrophobic materials will be particularly useful for typical aqueous wet casting. Useful agents include, without limitation, Stearic acid (Octadecanoic acid), Palmitic acid (Hexaecanoic acid), Magnesium stearate, Beeswax, Candelilla wax, Fatty acids and alcohols, Glycerl behenate, and Animal or plant waxes.

By "film" in this application, we expressly contemplate thin films, films, sheets and slabs, from a thickness of 0.01 mils to 100 mils.

Thus, the present invention provides a biocompatible film comprising a single layer having a plurality of components, the plurality of components having a predetermined (i.e., not random) non-uniform distribution in the thickness direction of the single layer. For example, one component can have a different concentration in the top and bottom or the top, middle and bottom layers of the film. The biocompatible film, and in particular the dosage unit of the biocompatible film, may have a substantially uniform distribution (i.e., varying less than 10%) in the longitudinal and lateral directions of the single layer. The present invention uses density differences in immiscible (and/or not completely soluble) component materials to cause a predetermined non-uniform distribution of at least one component in a cast or deposited film. The material(s) in, e.g., a cast or deposited film which is/are different in density and miscibility from the film former, forms/form a predetermined non-uniform distribution of such material(s) in the film after being cast. The component having the predetermined non-uniform distribution in the thickness direction of the single layer may be, without limitation, a bioactive absorption enhancer, an absorption retardant, a hydrophobic material, a bioactive agent, a stabilizer, anesthetics, buffer systems, aversives, dyes, a "friable" material like but not limited to certain acrylates etc. that will came apart to facilitate swallowing but release slowly, and any other material useful in the enhancement of the active. The component having the predetermined non-uniform distribution in the thickness direction of the single layer can also be a plurality of any of the foregoing materials, e.g., a plurality of bioactive agents. For example, a first bioactive can be provided in one domain and a second bioactive provided in another domain. For example, a precursor can be provided in one domain and the bioactive in another or multiple drugs can be provided in separate domains, etc.

As an example, a first bioactive agent may be provided in one portion (e.g., a top portion) in the thickness direction of the single layer and a second bioactive agent may be provided in another portion (e.g., a bottom portion) in the thickness direction of the single layer. The first bioactive agent may be absent from the another portion (e.g., the bottom portion) or present in a reduced amount while the second bioactive agent may be absent from the one portion (e.g., a top portion) or present in a reduced amount.

If the material(s) that is desired to have the non-uniform distribution is not naturally different in density and immiscible in the film former, hollow microspheres or other containment vessels such as cyclodextrins can be used to contain the material(s), alone or with ion exchange resins, to provide the requisite immiscibility/insolubility and/or density gradient required in this system.

Typical cyclodextrins are constituted by 6-8 glucopyranoside units, can be topologically represented as toroids with the larger and the smaller openings of the toroid exposing to the solvent secondary and primary hydroxyl groups respectively. Because of this arrangement, the interior of the toroids is not hydrophobic, but considerably less hydrophilic than the aqueous environment and thus able to host other hydrophobic molecules. In contrast, the exterior is sufficiently hydrophilic to impart cyclodextrins (or their complexes) water solubility. The natural $\alpha$-, $\beta$- and $\gamma$-cyclodextrin ($\alpha CD$, $\beta CD$ and $\gamma CD$) consist of six, seven, and eight glucopyranose units, respectively. The natural cyclodextrins, in particular $\beta CD$, are of limited aqueous solubility meaning that complexes resulting from interaction of lipophiles with these cyclodextrin can be of limited solubility resulting in precipitation of solid cyclodextrin complexes from water and other aqueous systems. In fact, the aqueous solubility of the natural cyclodextrins is much lower than that of comparable acyclic saccharides. This is thought to be due to relatively strong intermolecular hydrogen bonding in the crystal state. Substitution of any of the hydrogen bond forming hydroxyl groups, even by lipophilic methoxy functions, results in dramatic improvement in their aqueous solubility. Water-soluble cyclodextrin derivatives of commercial interest include the hydroxypropyl derivatives of $\beta CD$ and $\gamma CD$, the randomly methylated $\beta$-cyclodextrin (RM$\beta$CD), and sulfobutylether $\beta$-cyclodextrin sodium salt (SBE$\beta$CD).

In an oral delivery system, the release of the drug is either dissolution controlled, diffusion controlled, osmotically controlled, density controlled or pH-controlled. Cyclodextrins have been used as an excipient to transport the drugs through an aqueous medium to the lipophillic absorption surface in the gastro-intestinal tract, i.e., complexation with cyclodextrins has been used to enhance the dissolution rate of poorly water-soluble drugs. Hydrophilic cyclodextrins have been particularly useful in this regard. Rapid dissolving complexes with cyclodextrins have also been formulated for buccal and sublingual administration. In this type of drug delivery system, a rapid increase in the systemic drug concentration takes place along with the avoidance of systemic and hepatic first pass metabolism (Jain et al, 2002).

As known in art, nanoparticles can agglomerate unless in lipid media. According to the present invention a hydrophobic phase can be used for nanoparticles. In addition, many hollow spheres that can carry drug are only carried in lipid. According to the present invention, insulin can be placed into a sphere to protect it, and placed in a domain near the mucosa for mucosal absorption and the other film surface having retarded erosion and thus presenting the insulin from being swallowed and rendered inactive by the GI tract and first pass.

The bioactive agent of the present invention is preferably a pharmaceutical but may be any biological, antigen, confection, food, vitamin, botanical or nutraceutical, cosmaceutical, protein or genetic or other active agent Based on density and insolubility this method may also be used for the placement of radio tags and other analytical and marker sensors. See prior Fuisz U.S. Pat. No. 7,824,612, the contents of which are incorporated by reference in total here.

Examples of pharmaceutical bioactive agents include, but are not limited to ace inhibitors, such as Benazepril, Captopril, Enalapril, Lisinopril, Moexipril, Perindopril, Quinapril, Ramipril and Trandolapril; acne treatments, such as adapalene, azelaic acid, BenzaClin, Benzamycin, Benzoyl Peroxide, clindamycin, Duac, Erythromycin, Glycolic Acid, Isotretinoin, Insulin, Sulfacetamide with sulfur, Tazarotene and Tretinoin; actinic keratosis, such as declofenac, fluorouracil; addiction aids, such as buprenorphine, Disulfiram, Naltrexone, Suboxone and varenicline; aldosterone antagonists, such as eplerenone and spironolactone; alpha-1 adrenergic blockers, such as alfuzosin, doxazosin, prazosin, tamsulosin and terazosin; ALS agents, such as riluzole; Alzheimer's Disease medications, such as donepezil, Galantamine, rivastigmine, tacrine and memantine; anesthetics, such as dexmedetomidine, etomidate, ketamine, methohexital, pentobarbital, propofol and thiopental; angiotensin II receptor blockers, such as candesartan, eprosartan mesylate, irbesartan, losartan, olmesartan, telmisartin and valsartan; antacids, such as Aluminum hydroxide, AlOH and magnesium trisilicate; anti-arrhythmics, such as adenosine, amiodarone, Atropine, Bretylium, digoxin-Immune Fab, disopyramide, dofetilide, epinephrine, Esmolol, flecamide, ibutilide, isoproterenol, lidocaine, mexiletine, moricizine, procainamide, propafenone, quinidine, sotalol, tocamide and verapamil; antibiotics, such as Aztreonam, TMP/SMX, Chloramphenicol, Clindamycin, Dapsone, Daptomycin, Ertapenem, Imipenem/cilastatin, Linezolid, Meropenem, Metronidazole, Nitrofurantoin, Quinupristin/Dalfopristin, Rifaximin, Tigecycline, Telithromycin and Timidazole; anticholinergic acids, such as Dicyclomine, Donnatal, Flavoxate, Glycopyrrolate, Hyoscyamine, Oxybutynin, Propantheline and Tolterodine; anticonvulsants, such as carbamazepine, clonazepam, diazepam, ethosuximide, felbamate, fosphenyloin, gabapentin, levetiracetam, lamotrigine, lorazepam, Oxcarbazepine, Phenobarbital, phenyloin, pregabalin, primidone, tiagabine, topiramate and valproic acid; antidepressants, such as amitriptyline, buprorion, citalopram, desipramine, doxepin, duloxetine, escitalopram, fluoxetine, fluvoxamine, imipramine, mirtazapine, nefazodone, nortriptyline, nortriptyline, sertraline, trazodone and venlafaxine; anti-diarrheals, such as dephenoxylate+atropine, Imodium and bismuth subsalicylate; anti-emetics, such as Aprepitant, dolasetron, droperidol, granisetron, metoclopramide, ondansetron, prochlorperazine, scopolamine and trimethobenzamide; antifungals, such as Ampho B, Ampho B lipid, anidulafungin, caspofungin, Clotrimazole fluconazole, flucytosine, Griseofulvin, Itraconazole, ketoconazole, Micafungin, nystatin, Posaconazole, terbinafine, voriconazole, butenafine, ciclopirox, clotrimazole, enconazole, ketoconazole, Miconazole, naftifine, nystatin, oxiconazole terbinafine and Tolnaftate; anti-hepatitis, such as adefovir, entecavir, lamivudine, peginterferon alfa-2a, peginterferon alfa-2b, Rebetron and ribavirin; anti-herpetic agents, such as Acyclovir, famciclovir, valacyclovir, acyclovir, docosanol and penciclovir; antihistamines, such as cetirizine, desloratadine, fexofenadine, loratadine, chlorpheniramine, clemastine, cyproheptadine, dimenhydrinate, diphenhydramine, hydroxzine and promethazine; anti-hypertension, such as Benazepril & HCTZ, Captopril & HCTZ, Enalapril & HCTZ, Lisinopril & HCTZ, Moexipril & HCTZ, Losartan & HCTZ, Valsartan & HCTZ, Atenolol & chlorthalidone, Bisoprolol & HCTZ, Metoprolol & HCTZ, Nadolol & bendroflumethazide, Propranolol & HCTZ, Timolol & HCTZ, Amlodipine & benazepril, Verapamil & trandolapril, Amiloride & HCTZ, Spironolactone & HCTZ, Triamterene & HCTZ, Clonidine & chlorthalidone, Hydralazine & HCTZ, Methyldopa & HCTZ and Prazosin & polythiazide; anti-hypertensives, such as Aliskiren, Aliskiren, epoprostenol, fenoldopam, hydralazine, minoxidil, nitroprusside, phentolamine and treprostinil; anti-influenza agents, such as amantadine, oseltamivir phosphate, rimantadine and zanamivir; anti-malarials/anti-protozoals/amebicides, such as Atovaquone, Chloroquine, Iodoquinol, Mefloquine, Primaquine, Pyrimethamine, Pyrimethamine-Sulfadoxine and Quinine Sulfate; anti-platelet agents, such as abciximab, dipyridamole/ASA, anagrelide, cilostazol, clopidogrel, dipyridamole, eptifabatide, ticlopidine and tirofiban; antipsychotics, such as aripiprazole, chlorpromazine, Clozapine, fluphenazine, haloperidol, loxapine, molindone, olanzepine, perphenazine, pimozide, quetiapine, risperidone, thioridazine, thiothixine, trifluoperazine, ziprasidone and Lithium; antispasmotics, such as Dicyclomine, Donnatal Extentabs, Propantheline, Simethicone, hyoscyamine, Librax, tegaserod and Bellergal-S; anti-tussives/expectorants, such as Benzonatate and guaifenesin; atopic dermatitis medications, such as pimecrolimus and tacrolimus; benzodiazepines and non-benzodiazepine sedatives, such as alprazolam, buspirone, chlordiazepoxide, chlorazepate, clonazepam, diazepam, estazolam, eszcpiclone, flurazepam, lorazepam, midazolam, Oxazepam, rameleton, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol and timolol; bile acid sequestrants, such as cholestyramine, colesevelam and colestipol; bisphosphonates, such as alendronate, etidronate, pamidronate, risedronate, tiludronate and Zoledronic acid, Raloxifene and Teriparatide; bladder spasm medications, such as flavoxate, hyoscyamine, darifenacin, oxybutynin, solifenacin, tolterodine and trospium; benign prostatic hypertrophy medications, such as alfuzosin, doxazosin, dutasteride, finasteride, tamsulosin and terazosin; burn preparations, such as mafenide acetate and silver sulfadiazine; calcium channel blockers, such as amlodipine, bepridil, diltiazem, felodipine, isradipine, nicardipine, nifedipine and nisoldipine; calcium supplements, such as Calcium and Hypocalcemia; cephalosporins, such as Cefadroxil, Cefazolin, Cephradine, Cephalexin, Cefaclor, Cefotetan, Cefoxitin, Cefprozil, Cefuroxime, Cefuroxime, loracarbef, Cefdinir, Cefixime, Cefoperazone, Cefotaxime, Cefpodoxime, Ceftazidime, Ceftibuten, Ceftizoxime and Cefepime; colony stimulating factors, such as darbepoietin alfa, erythropoietin, filgrastim, oprelvekin, pegfilgrastim and sargramostim; corticosteroids, such as Budesonide, cortisone acetate, dexamethasone, fludrocortisones, hydrocortisone, methylprednisolone and prednisone; corticosteroids Intra-articular, such as Depo-Medrol and Triamcinolone Acetonide; cystitis, such as pentosan polysulfate, Bethanecol and Alum irrigation; decongestants, such as Phenylephrine and Pseudoephedrine; anti-diabetic agents, such as acarbose, Miglitol and metformin, Avandamet®, Glucovance, Metaglip, Metaglip, rosiglitazone, osiglitazone, repaglinide, Chlorpropamide, glimepiride, glyburide, glipizide, Tolazamide, Tolbutamide, Glucagon, extenatide and pramlintide; direct thrombin inhibitors, such as argatroban, Bivalirudin and lepirudin; disease modifying agents, such as adalimumab, anakinra, auranofin, azathioprine, etanercept, hydroxychloroquine, infliximab, leflunomide, methotrexate and sulfasalazine; diuretics, such as Acetazolamide, Amiloride, Amiloride and HCTZ Bendroflumethiazide, Bumetanide, Chlorothiazide, Chlorthalidone, Dichlorphenamide, Eplenerone, Ethacrynic acid, Furosemide, Hydrochlorothiazide, HCTZ/Triampterene, Hydroflumethiazide, Indapamide, Methazolamide, Methyclothiazide, Methyclothiazide, Metolazone, Polythiazide, Spironolactone, Spironolactone, HCTZ Torsemide, Trichlormethiazide and Triamterene; endocrine agents, such as bromoc cinacalcet cosyntropin, riptine, cabergoline, calcitonin, desmopressin, Leuprolide, octreotide and vasopressin; erectile dysfunction agents, such as Sildenafil, tadalafil, vardenafil; fever medications, such as allopurinol, antihistamines, azathioprine, barbiturates, carbamazepine, cephalosporins, cimetidine, folic acid, hydralazine, hydroxyurea, ibuprofen, isoniazid, methyldopa, nitrofurantoin, penicillins, phenyloin, phenyloin, procainamide, prophylthiouracil, quinidine, streptomycin sulfonamides, sulindac, triamterene and vancomycin; fibrates, such as clofibrate, fenofibrat and gemfibrozil; fluoroquinolones, such as Ciprofloxacin, Gatifloxacin, Levofloxacin, Moxifloxacin, Norfloxacin and Ofloxacin; gastrointestinal agents, such as Alosetron, infliximab, Mesalamine, misoprostol, Neomycin, octreotidev, osalazine, Orlistat, sucralafate, Sulfasalazine and vasopressin; gout treatments, such as allopurinol, colchicine, probenecid, Rasburicase and sulfinpyrazone; H2 receptor blockers, such as cimetidine, famotidine, nizatidine and ranitidine; aAnti-herpetic agents, such as Acyclovir, famciclovir, valacyclovir, acyclovir, docosanol and penciclovir; hypertensive urgency, such as Captopril, Clonidine and Labetalol; hypertensive emergency, such as Enalaprilat, Esmolol, Fenoldopam mesylate, Hydralazine, Labetalol, Nicardipine, Nitroglycerin and Sodium nitroprusside; hemorrhoidal preparations, such as Anusol HC, Anusol Suppository, Dibucaine, pramoxine 1%, Proctofoam-HC and Analpram-HC; inflammatory bowel disease agents, such as balsalazide, budesonide, infliximab, mesalamine, olsalazine and sulfasalazine; Interferon, such as Interferon Alfa-2A, Interferon Alfa-2b, Interferon Alfa-2b and Ribavirin combo Pack, Interferon Alfa-N3, Interferon Beta-1A, Interferon Beta-1B (Betaseron); intermittent claudication, such as cilostazol and pentoxifylline; immunizations, such as Comvax, diphtheria-tetanus toxoid, Hepatitis A vaccine, Hepatitis B vaccine, Influenza vaccine, Fluzone, Lyme disease vaccine, PNEUMOVAX* 23; laxatives, such as Bisacodyl, Cascara, Docusate, Fleet Phospho-Soda, Glycerin, Lacalutose, lubiprostone, Magnesium citrate, Magnesium hydroxide—MOM, Mineral Oil, Pericolace, Psyllium and Senna; low molecular weight heparins, such as dalteparin, danaparoid, enoxaparin, tinzaparin, fondaparinux; macrolides, such as Azithromycin, Clarithromycin and Erythromycin; magnesium, such as magnesium salt; migraine treatments, such as almotriptan, eletriptan, frovatriptan, naratriptan, rizatriptan, sumatriptan, zolmitriptan, Cafergot®, Cafergot®, dihydroergotamine and Midrin®; mouth and lip treatments, such as amlexanox, Benzocaine, carbamide, peroxide, Kenalog in Orabase®, Phenol, chlorhexidine gluconate, clotrimazole, Nystatin, Penciclovir, docosanol, Gelclair, lidocaine viscous, BMX Cocktail, Pilocarpine and Artificial saliva; multiple sclerosis treatments, such as glatiramer, interferon beta-1A and interferon beta-1B; muscle relaxants, such as baclofen, carisprodol, cyclobenzaprine, cyclobenzaprine, Diazepam, Metaxalone, Methocarbamol, Orphenadrine; nasal preparations, such as azelastine, beclomethasone, budesonide, cromolyn, desmopressin acetate, flunisolide, fluticasone, Ipratropium bromide, mometasone, oxymetazoline, phenylephrine, Saline nasal spray, Sumatriptan, triamcinolone and Zolmitriptan; urology treatments, such as Belladonna and opium, flavoxate, hyoscyamine, hyoscyamine, oxybutynin, solifenacin, tolterodine and trospium; neuromuscular blockers, such as Atracurium, Cisatracurium, doxacurium, mivacurium, pancuronium, Rocuronium, Succinylcholine, vecuronium, Mivacurium, Rapacuronium, Rocuronium, Succinylcholine, Atracurium, Cisatracurium, Pancuronium, Vecuronium, Doxacurium, Pipecuronium and Tubocurarine; nitrates, such as Isosorbide dinitrate, Isosorbide mononitrate, Nitroglycerin ointment, Nitrobid and Nitroglycerin transdermal; NSAID's, such as Arthrotec, diclofenac, Etodolac, indomethacin, Ketorolac, Sulindac, Tolmentin Diflunisal Salsalate Meloxicam, piroxicam, Nabumetone Flurbiprofen, Ibupropen, Ketoprofen, Naproxen, Oxaprozin, celecoxib, Rofecoxib and Valdecoxib; ophthalmic agents, such as, proparacaine, tetracaine, Ciprofloxacin, Erythromycin, Gentamcyin, levofloxacin, levofloxacin, norfloxacin, Ofloxacin, Polysporin®, Polytrim, Sulfacetamide, Tobramycin, Blephamide®, Blephamide®, Maxitrol®, Pred G® and TobraDex®, Dexamethasone, Fluorometholone, Loteprednol, Prednisone, Rimexolone, azelastine, Cromolyn sodium, emedastine, Epinastine, Ketotifen Fumarate Ophthalmic Solution 0.025%, Levocabastine, Lodoxamide tromethamine, Naphazoline, Naphcon-A®, nedocromil, Olopatadine, pemirolast, Betaxolol, Betaxolol, Levobunolol, Timolol, Brinzolamide, Dorzolamide, Pilocarpine, bimatoprost, Latanoprost, travoprost, unoprostone, Apraclonidine, Brimonidine, Cosopt® and Cosopt®, Atropine, Cyclopentolate, Homatropine, Phenylephrine, Phenylephrine, Diclofenac, Flurbiprofen and Ketorolac; ear (otic) preparations, such as Auralgan®, carbamide peroxide, CIPRODEX®, Ciprofloxacin and hydrocortisone, Cortisporin®, Ofloxacin, Triethanolamine and Vosol Otic®; opiates, such as Codeine Fentanyl Hydrocodone Hydrocodone, Meperidine Methadone, morphine, xycodone, Propoxyphene, Darvon®, Fioricet, Fiorinal, Soma compound, Tramadol, Anexsia, Darvocet, Darvon Compound, Lorcet, Lortab, Percocet, Percodan, Roxicet, Tylenol with Codeine, Tylox, Vicodin, Wygesic, Buprenorphene, Butorphanol, Dezocine, Nalbuphine, Pentazocine, Nalmefene Naloxone, Suboxone® and Ziconotide; parkinson's disease treatments, such as amantadine, benztropine, bromocriptine, entacapone, pergolide, pramipexole, ropinirole, selegiline, Sinemet®, tolcapone and trihexyphenidyl; PCA—Patient Controlled Analgesia, such as Fentanyl, Hydromorphone, Meperidine and Morphine; penicillin's, such as Ampicillin, Ampicillin/sulbactam, Amoxicillin, Amoxicillin/Clavulanate, Cloxacillin, Dicloxacillin, Nafcillin, Penicillin G, Penicillin VK, Piperacillin, Piperacillin/Tazobactamm, Ticarcillin, and Ticarcillin/Clavulanate; phosphate supplementation, such as, K-Phos® Neutral Tablets, K-PHOS® ORIGINAL, NeutraPhos®; potassium supplementation, such as K-LOR, Klor-Con®, Potassium depletion; prostate cancer medications, such as bicalutamide, flutamide, goserelin, leuprolide and nilutamide; proton pump inhibitor's, such as esomeprazole, Lansoprazole, Omeprazole, Pantoprazole and Rabeprazole Sodium; psoriasis medications, such as acitretin, alefacept, Anthralin, Calcipotriene, efalizumab and Tazarotene; renal failure medications, such as Aluminum Hydroxide, Calcium acetate, Calcitriol, Doxercalciferol, Ferric Sodium Gluconate, paricalcitol and sevelamer; pulmonary medications, such as ipratropium, tiotropium, albuterol, bitolterol, levalbuterol, pirbuterol, metaproterenol, formoterol, salmeterol, Advair®, Symbicort®, beclomethasone, budesonide, flunisolide, fluticasone, Mometasone furoate, triamcinolone, montelukast Singulair®, zafirlukast, cromolyn sodium, nedocromil, acetylcysteine and aminophylline/theophylline; disease modifying agents, such as adalimumab, anakinra, auranofin, azathioprine, etanercept, hydroxychloroquine, infliximab, leflunomide, methotrexate and sulfasalazine; HMG COA reductase inhibitors, such as Atorvastatin, Fluvastatin, Lovastatin, Pravastatin, Rosuvastatin, Simvastatin, Advicor®, Vytorin® and ezetimibe; stimulants, such as atomoxetine, benzphetamine, Caffeine, dexmethylphenidate, Dextroamphetamine, diethylpropion, Methylphenidate, Modafinil, Pemoline, phendimetrizine, phentermine and sibutramine; tetracyclines such as Doxycycline, Minocycline and Tetracycline; thrombolytic agents such as Alteplase; anti-thyroid agents such as methimazole and propylthiouracil; toxicology related medications such as acetylcysteine, Charcoal, deferoxamine, digoxin immune fab, flumazenil, fomepizole, methylene blue, naloxone, sodium polystyrene sulfonate and Sorbitol; anti-mycobacterial agents such as Ethambutol, Isoniazid, Pyrazinamide, rifabutin, Rifamate, Rifampin, Rifapentine and Rifater; topical products such as Alitretinoin, Becaplermin, Calamine, Capsaicin, Doxepin, lidocaine/prilocalne, fluorouracil, Masoprocol, Pimecrolimus, Selenium sulfide and Tacrolimus; topical anti-viral agents such as acyclovir, docosanol, imiquimod, penciclovir, podofilox and podophyllin; topical antibacterials such as bacitracin, metronidazole, mupirocin, bacitracin/neomycin/polymyxin, bacitracin/polymyxin and silver sulfadiazine; topical antifungals such as butenafine, ciclopirox, clotrimazole, econazole, ketoconazole, miconazole, naftifine, nystatin, oxiconazole, terbinafine and tolnaftate; topical anti-parasitic agents such as Crotamiton, Lindane, Permethrin, pyrethrins and piperonyl butoxide; topical burn preparations such as mafenide acetate and silver sulfadiazine; topical corticosteroids such as Aclometasone diproprionate, Desonide, Flucinolone acetonide, Hydrocortisone, Betamethasone dipropionate, betamethasone valerate, clocortolone pivalate, desoximetasone, fluocinolone acetonide, flurandrenolide, fluticasone propionate, Chydrocortisone butyrate, hydrocortisone valerate, mometasone furoate, prednicarbate, triamcinolone, amcinonide, augmented betamethasone dipropionate, betamethasone dipropionate, desoximetasone, diflorasone diacetate, fluocinolone acetonide, fluocinonide, halcinonide, clobetasol propionate, diflorasone diacetate and halobetasol propionate; urology medications such as pentosan polysulfate, Bethanecol and phenazopyridine; vaginal preparations such as clindamycin, metronidazole, butoconazole, clotrimazole, miconazole, terconazole and tioconazole; vasodilators such as Fenoldopam mesylate, Hydralazine, Nesiritide, Nicardipine, Nitroglycerin, and Sodium Nitroprusside; and vasopressors and inotropes such as Dobutamine, Dopamine, Epinephrine, inaminone, Milrinone, Norepinephrine, Phenylephrine, and Vasopressin, insulin and other peptides, hormones and other contraceptives and nicotine.

Examples of food or nutraceutical bioactive agents include, but are not limited to, constituents in foods or dietary supplements that are responsible for changes in health status, such as components of plants, especially fruits and vegetables, e.g., soy which contains isoflavones and phytoestrogens, tomatoes which contain lycopene that may have anticancer properties, berries such as blueberries and raspberries which contain flavonoids like anthocyanins that may act as antioxidants, green tea which contains epigallocatechin gallate (EGCG) that may have anticancer properties, resveratrol from red grape products as an antioxidant, soluble dietary fiber products, such as psyllium seed husk for reducing hypercholesterolemia, broccoli (sulforaphane) as a cancer preventative, and soy or clover (isoflavonoids) to improve arterial health. Flavonoids, antioxidants, alpha-linolenic acid from flax seeds, extracts such as ginseng, garlic oil, etc.

Examples of biological bioactive agents include, but are not limited to biologically active substances in plants that have proven (e.g. cholesterol lowering effects of phytosterols) or potential beneficial effects on health, i.e., phytochemicals or phytonutrients, in particular phytochemicals in leaves, stems, roots, tubers, buds, fruits, seeds and flowers, and plant derived foods and drinks (such as tea, coffee, alcoholic beverages), such as flavonoids found in a range of plant derived foods including tea, wine, onions, apples and berries, glucosinolates from Cruciferous vegetables, phenolic acids in tea and coffee for example, and carotenoids (some of which are precursors of vitamin A) prevalent in red, green and orange fruits and vegetables.

Examples of antigen bioactive agents include, but are not limited to exogenous antigens, endogenous antigens, autoantigens and tumor antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells (CD4.sup.+) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic CD8.sup.+ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. An autoantigen is usually a normal protein or complex of proteins (and sometimes DNA or RNA) that is recognized by the immune system of patients suffering from a specific autoimmune disease. These antigens should, under normal conditions, not be the target of the immune system, but, due to mainly genetic and environmental factors, the normal immunological tolerance for such an antigen has been lost in these patients. Tumor antigens or Neoantigens are those antigens that are presented by MHC I or MHC II molecules on the surface of tumor cells. These antigens can sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens can also be on the surface of the tumor in the form of, for example, a mutated receptor, in which case they will be recognized by B cells.

Examples of botanical bioactive agents include, but are not limited to PMI-004 (advanced botanical formulation for type II diabetes—Represents a multi-mechanism bioactive that: 1) in adipocytes increases adiponectin secretion, 2) in the liver lowers PEPCK expression, and 3) in muscle cells increases cellular signaling through the insulin receptor pathway, increasing glucose uptake, glycogen synthase, and glycogen accumulation.), PMI-005 (botanical bioactive, derived from a common vegetable, that inhibits gene expression of a variety of pro-inflammatory cytokines (including a-TNF, i-NOS, IL-1b, and COX-2), currently undergoing a human clinical trial in osteoarthritis. Also may have utility in the management of severe/life threatening inflammatory conditions, such as in the management of the septic patient.), PMI-006 (botanical bioactive, derived from a spice, that inhibits a range of inflammation-related enzymes (including a-TNF and COX-2). Also possesses range of novel bioactivities related to both lipid and glucose metabolism (RXR receptors).), PMI-007 (a powerful, centrally acting, botanical appetite suppressor which acts via a unique central pathway in the nutrient-sensing hypothalamic neurons by increasing ATP content/production. It possesses potent anorectic activity without typical CNS appetite suppressor side effects. Pre-clinical data has shown that the agent suppresses both appetite and reduces weight in animal models, while there is supporting clinical evidence of human efficacy.), PMI-008 (botanical bioactive, derived from an agricultural waste processing stream, that blocks fat accumulation/absorption and promotes weight loss via interaction with a variety of lipases including PL, LPL, and HSL.), PMI-016 (a powerful, plant-derived anabolic/ergogenic agent, with no androgenic side effects; could be used in a range of human muscle wasting disorders, including those associated with both cancer and AIDS, as well as general aging (sarcopenia). This agent has been shown to induce protein synthesis in muscle cells (similar to IGF) and promote a reduction in protein degradation, while it has also been shown to increase growth hormone gene transcription and decrease in ubiquitin protein ligase gene transcription. PMI-016 shows no binding to testosterone receptor in contrast to anabolic steroids.), tobacco and tobacco products.

The bioactive can be one or more vitamins, e.g., Vitamin D, Vitamin E, Vitamin K, Vitamin B12, Riboflavin, Vitamin B6, Thiamine, Niacin, and Biotin. Since the film of the present invention can have a non-uniform distribution of fatty materials, this allows for the inclusion of fat soluble and water soluble vitamins all into one film.

The FDA defines drugs as products that "cure, treat, mitigate or prevent disease or that affect the structure or function of the human body." Cosmetic products are defined by the FDA as "articles intended to be rubbed, poured, sprinkled, or sprayed on, introduced into, or otherwise applied to the human body . . . for cleansing, beautifying, promoting attractiveness, or altering the appearance." Although cosmaceutical products have properties of both groups, the FDA lumps them under the definition of cosmetics, and they are not recognized as a distinct category. Because cosmaceutical products are not included in the FDA's definition of drugs, they are not subject to the same regulations, restrictions, and testing.

This same inventive step involving the use of immiscibility/solubility and density differential can be used to concentrate bioactive absorption enhancers in a layer on the side if the dosage unit with proximity to the mucosal surface The film of the present invention can also include a mucosal absorbing enhancer, i.e., a substance that enhances absorption through the mucosa, mucosal coating and epithelium (otherwise known (see U.S. Patent Application Publication No. 2006/0257463) as a "penetration enhancer" or "permeability enhancer"). The mucosal absorbing enhancer may include but is not limited to polyethylene glycol (PEG), diethylene glycol monoethyl ether (Transcutol), 23-lauryl ether, aprotinin, azone, benzalkomin chloride, cetylperidium chloride, cetylmethylammonium bromide, dextran sulfate, lauric acid, lauric acid/propylene glycol, lysophosphatilcholine, menthol, methoxysalicylate, oleic acid, phosphaidylcholine, polyoxyethylene, polysorbate 80, sodium EDTA, sodium glycholated, sodium glycodeoxycholate, sodium lauryl sulfate, sodium salicylate, sodium taurocholate, sodium taurodeoxycholate, sulfoxides, and various alkyl glycosides or, as described in U.S. Patent Application Publication No. 2006/0257463, bile salts, such as sodium deoxycholate, sodium glycodeoxycholate, sodium taurocholate and sodium glycocholate, surfactants such as sodium lauryl sulfate, polysorbate 80, laureth-9, benzalkonium chloride, cetylpyridinium chloride and polyoxyethylene monoalkyl ethers such as the BRIJ® and MYRJ® series, benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, alginates, cyclodextrins, the sulfoxides, such as dimethyl sulfoxide and dodecyl methyl sulfoxide, the terpenes, such as menthol, thymol and limonene, urea, chitosan and other natural and synthetic polymers. Preferably, the mucosal absorbing enhancer is a polyol, e.g., polyethylene glycol (PEG), glycerin, maltitol, sorbitol etc. or diethylene glycol monoethyl ether (Transcutol).

A plasticizer may also be included. The plasticizer may be present in an amount up to 30% based on the weight of the thermoplastic polymer, or present to as low a range as to be non present. The plasticizer can be, without limitation, at least one of polyethylene oxide, polypropylene glycol, polyethylene glycol, glycerin, edible polyols, glycerol, polyols, maltitol, isomalt, and reduced sugars. The use of certain plasticizers may function to increase mucoadhesion (e.g. polypropylene glycol or glycerin) and may be used for this purpose.

A coloring agent can optionally be added. The use of titanium dioxide will create a white product. Other edible pigments may be used, such as Colorcon Red #40. The coloring can also be multilayered by taking advantage of the rheological differences of the layers of the film relative to the solubility and/or density of the coloring material.

A range of film formers may be used to make the film of the present invention. Such film formers may include, without limitation, water soluble, water insoluble, or a combination of one or more either water soluble or water insoluble polymers. The polymer may include cellulose or a cellulose derivative. Specific examples of useful water soluble polymers include, but are not limited to, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

Other polymers useful for incorporation into the films including but not limiting, of the present invention include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(.alpha.-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of polyurethane and poly(lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338.degree.-347.degree. F. (170.degree.-175.degree. C.); lactide/glycolide 100 L, believed to be 100% glycolide having a melting point within the range of 437.degree.-455.degree. F. (225.degree.-235.degree. C.); lactide/glycolide 85/15, believed to be 85% lactide and 15% glycolide with a melting point within the range of 338.degree.-347.degree. F. (170.degree.-175.degree. C.); and lactide/glycolide 50/50, believed to be a copolymer of 50% lactide and 50% glycolide with a melting point within the range of 338.degree.-347.degree. F. (170.degree.-175.degree. C.).

The Biodel materials represent a family of various polyanhydrides which differ chemically and generally regarded as biocompatible.

Example A

Solutions Chart

| Solution | Polymer | % weight |
|---|---|---|
| C | CMC | 5% |
| D | CMC | 2.5% |
| E | HEC | 1% |
| F | MC | 2% |
| G | PVP | 5% |
| H | HPMC | 2% |
| J | HPMC | 1% |

Solutions were made of the above chart, employing room temperature water. The polymers in each case were mixed in and allowed to hydrate.

In the above chart, CMC means Carboxymethyl cellulose, HEC means hydroxy ethyl cellulose, MC means methyl cellulose, PVP means polyvinylpyrrolidone; HPMC means Hydroxypropyl methylcellulose, and PS means Polysorbate.

Employing these solutions, film matrices were then made in accordance with the chart below.

| Film identifier | Solution | Solution Mass (g) | Stearic Acid (g) | Compritol 888 ATO (g) | Magnesium Stearate | PS 20 | % w hydrophobic |
|---|---|---|---|---|---|---|---|
|  | C | 2.7856 |  | .0636 |  |  | 2.2 |
|  | C | 2.58 | 0.057 |  |  |  | 2.2 |
|  | E | 3.313 | 0.074 |  |  |  | 2.2 |
|  | E | 3.2241 | 0.0756 |  |  | 0.05 | 2.3 |
|  | E | 4.4428 |  | .2531 |  |  | 5.3 |
|  | E | 3.2868 |  | 0.0496 |  |  | 1.5 |

-continued

| Film identifier | Solution | Solution Mass (g) | Stearic Acid (g) | Compritol 888 ATO (g) | Magnesium Stearate | PS 20 | % w hydrophobic |
|---|---|---|---|---|---|---|---|
| Film Y | C | 2.3989 |  | 0.0579 |  |  | 2.4 |
| Film X | C | 2.5268 |  |  | 0.0521 |  | 2.0 |
|  | H | 5.1406 |  | 0.13 |  |  | 2.5 |
|  | H | 5.9568 | 0.1962 |  |  |  | 3 |
|  | J | 6.4501 |  | 0.1773 |  |  | 2.7 |

After the recipes were made, the material was cast on glass using a plastic lid to spread the material. The films were then placed in a moisture balance and heated to 120 degrees C. until they reach a steady mass equilibrium and then they were removed from the oven and allowed to cool to room temperature.

The resulting films ranged from approximately 2 to 4 mils.

The purpose of this experiment was to create hydrophobic domains in the resulting films.

To demonstrate this, films cut from the film made with CMC with glyceryl behenate (Compritol 888 ATO) were tested, i.e. Film "X."

The films were placed on a flat surface with the hydrophobic side up, and a drop of water was placed on top of each film and the films were examined initially and at time point one minute as a measure of contact angle. Then, films from the same film samples were placed hydrophobic side down and again, a drop of water was placed on top of each film and the films were examined at time point one minute.

The results of this experiment demonstrated vividly that the lower density top side of the film was indeed the hydrophobic side and very slow to wet, whereas the opposite side of the film was the non-hydrophobic side, relatively quick to wet like a conventional film.

A similar test with similar results was conducted with films cut from the film made with CMC and magnesium stearate, i.e. Film "Y."

This experience validated the invention. Using a conventional film casting process, films were made with a resulting domain region—due to immiscibility, solubility and density differences—with slow dissolution characteristics. These domains formed at the top of the non uniform component thin cast film. The benefits of this invention, to reduce salivary flow, and improve absorption at the desired side are discussed above.

Example B

Two samples of the Film Y (from the Example above) above here cut in equal sizes, i.e. 9 mm*19 mm. These two samples were measured on a balance for mass and the results were 140 mg and 141 mg—less than a 1% difference. Thus, the content uniformity—when comparing one dosage unit to another of two films with geographic domains—was confirmed.

We claim:

1. A self-supporting biocompatible film comprising a single layer having a plurality of components, at least one of the plurality of components having a predetermined non-uniform distribution in the thickness direction of the single layer.

2. The self-supporting biocompatible film according to claim 1, wherein the plurality of components include a bioactive agent.

3. The self-supporting biocompatible film according to claim 2, wherein the bioactive agent is present throughout the thickness of the single layer.

4. The self-supporting biocompatible film according to claim 3, wherein the bioactive agent has a substantially uniform distribution in the thickness direction of the single layer.

5. The self-supporting biocompatible film according to claim 3, wherein the bioactive agent has a substantially non-uniform distribution in the thickness direction of the single layer.

6. The self-supporting biocompatible film according to claim 2, wherein the bioactive agent is at least one material selected from the group consisting of a pharmaceutical, a biological, an antigen, a confection, a food, a vitamin, a botanical, a nutraceutical, a cosmaceutical, a protein and a genetic.

7. The self-supporting biocompatible film according to claim 2, wherein a first bioactive agent is provided in one portion in the thickness direction of the single layer and a second bioactive agent is provided in another portion in the thickness direction of the single layer.

8. The self-supporting biocompatible film according to claim 2, wherein the bioactive agent is insulin.

9. The self-supporting biocompatible film according to claim 2, wherein the at least one component having the predetermined non-uniform distribution in the thickness direction of the single layer is a bioactive absorption enhancer.

10. The self-supporting biocompatible film according to claim 2, wherein the at least one component having the predetermined non-uniform distribution in the thickness direction of the single layer is a hydrophobic material.

11. The self-supporting biocompatible film according to claim 2, wherein the bioactive agent is selected from the group consisting of nicotine, tobacco and tobacco derived botanical agents.

12. A self-supporting biocompatible film comprising a single layer having a plurality of components, at least one of the plurality of components having a non-uniform distribution in the thickness direction of the single layer and a substantially uniform distribution in the longitudinal and lateral directions of the single layer.

13. The self-supporting biocompatible film according to claim 12, wherein the plurality of components include a bioactive agent.

14. The self-supporting biocompatible film according to claim 13, wherein the bioactive agent is present throughout the thickness of the single layer.

15. The self-supporting biocompatible film according to claim 14, wherein the bioactive agent has a substantially uniform distribution in the thickness direction of the single layer.

16. The self-supporting biocompatible film according to claim 14, wherein the bioactive agent has a substantially non-uniform distribution in the thickness direction of the single layer.

17. The self-supporting biocompatible film according to claim 13, wherein the bioactive agent is at least one material selected from the group consisting of a pharmaceutical, a biological, an antigen, a confection, a food, a flavor, a vitamin, a botanical, a nutraceutical, a cosmaceutical, a protein and a genetic agent or modifier.

18. The self-supporting biocompatible film according to claim 13, wherein a first bioactive agent is provided in one portion in the thickness direction of the single layer and a second bioactive agent is provided in another portion in the thickness direction of the single layer.

19. The self-supporting biocompatible film according to claim 13, wherein the bioactive agent is insulin.

20. The self-supporting biocompatible film according to claim 13, wherein the at least one component having the predetermined non-uniform distribution in the thickness direction of the single layer is a bioactive absorption enhancer.

21. The self-supporting biocompatible film according to claim 13, wherein the at least one component having the predetermined non-uniform distribution in the thickness direction of the single layer is a hydrophobic material.

22. The self-supporting biocompatible film according to claim 13, wherein the bioactive agent is selected from the group consisting of nicotine, tobacco and tobacco derived botanical agents.

23. A self-supporting biocompatible film dosage unit comprising a single layer having a plurality of components, at least one of the plurality of components having a non-uniform distribution in the thickness direction of the single layer and a substantially uniform distribution in the longitudinal and lateral directions of the single layer.

24. The self-supporting biocompatible film dosage unit according to claim 23, wherein the plurality of components include a bioactive agent.

25. The self-supporting biocompatible film dosage unit according to claim 24, wherein the bioactive agent is present throughout the thickness of the single layer.

26. The self-supporting biocompatible film dosage unit according to claim 25, wherein the bioactive agent has a substantially uniform distribution in the thickness direction of the single layer.

27. The self-supporting biocompatible film dosage unit according to claim 25, wherein the bioactive agent has a substantially non-uniform distribution in the thickness direction of the single layer.

28. A method of making a self-supporting biocompatible film comprising the steps of:
depositing a fluid composition on a substrate, the fluid composition including a film forming material and at least one other component immiscible with the film forming material and having a density different than the film forming material into a single layer,
drying the single layer such that the at least one other component has a predetermined non-uniform distribution in the thickness direction of the single layer after drying, and removing the single layer after drying from the substrate.

29. The method according to claim 28, wherein the step of drying the single layer is delayed for a predetermined period of time after completion of the step of depositing the fluid composition.

30. The method according to claim 29, wherein the predetermined period of time is 0.001 second to 2 minutes.

31. The method according to claim 29, wherein the predetermined period of time is 0.001 to 1.5 minutes.

* * * * *